United States Patent [19]

Ichihashi et al.

[11] Patent Number: 5,202,709
[45] Date of Patent: Apr. 13, 1993

[54] OPHTHALMOLOGICAL ALIGNMENT AND MEASUREMENT APPARATUS

[75] Inventors: Tadashi Ichihashi, Tokyo; Takashi Hirano, Shiki, both of Japan

[73] Assignee: Kowa Company Ltd., Japan

[21] Appl. No.: 662,786

[22] Filed: Feb. 28, 1991

[30] Foreign Application Priority Data

Mar. 14, 1990 [JP] Japan ................. 2-61178

[51] Int. Cl.⁵ .......................... A61B 3/14; A61B 3/10
[52] U.S. Cl. ........................... 351/208; 351/221
[58] Field of Search ............... 351/205, 214, 221, 208; 128/633, 745; 606/4

[56] References Cited

U.S. PATENT DOCUMENTS 4,838,679 6/1989 Bille ........................... 351/221 X Primary Examiner—Rodney B. Bovernick
Attorney, Agent, or Firm—Bruce L. Adams; Van C. Wilks

[57] ABSTRACT

An ophthalmological measurement apparatus wherein the interior of a patient's eye is irradiated with a laser beam and the scattering of the laser beam is measured to determine protein concentration in the oculi anterior. The apparatus is provided with scanning means for scanning the measurement zone during alignment of the eye as well as during measurement. During alignment the measurement zone is scanned at high speed by the laser beam and at the same scanning width as the scanning width used during measurement, and the signal obtained from the photosensor at this time is processed to provide information on and an indication of the appropriateness of the state of alignment. This makes it possible to observe any harmful light rays that will actually appear during measurement.

15 Claims, 5 Drawing Sheets

OPHTHALMOLOGICAL ALIGNMENT AND MEASUREMENT APPARATUS

BACKGROUND OF THE INVENTION

1. Field of the Invention

This invention relates to an ophthalmological measurement apparatus, and more particularly to an ophthalmological measurement apparatus which irradiates the interior of a patient's eye with a beam of laser light and uses the laser beam scattered from the interior of the eye to output measurement quantities such as the protein concentration in the oculi anterior.

2. Description of the Prior Art

Measurement of protein concentration in the oculi anterior is of considerable importance in determining whether the camera oculi is inflamed, that is, whether the blood-aqueous barrier function is normal or not. In one method that is frequently used for this, a slit lamp microscope is employed to grade the concentration by observation with the naked eye, while in another method photographic techniques are used to obtain quantitative measurements. However, as yet there is no method that is easy to use clinically.

Data obtained with the conventional method of naked-eye measurement lacks reliability as judgments vary depending on the person making the measurement. One solution has been to use a method in which a beam of laser light is projected into the eye and the light scattering from the eye is detected and subjected to quantitative analysis.

Examples of such an ophthalmological measurement apparatus which irradiates the eye with a beam of laser light and detects the light scattered from the eye are disclosed in Japanese Patent Public Disclosures Nos. 120834/87 (corresponding to U.S. Pat. No. 4,957,360) and 135128/88 (corresponding to U.S. patent application Ser. No. 111,014 filed on Oct. 20, 1987). In such an arrangement, the beam from a laser light source is focused on a prescribed point in the eye such as in the oculi anterior, for example, and scattered light from the eye is detected, via a mask with a rectangular aperture of a prescribed size, by a photosensor which converts the light to an electrical signal which is processed to determine the protein concentration in the oculi anterior or other such ophthalmological measurement quantities.

The extremely low intensity of the scattered laser light makes it susceptible to noise in the form of light other than light from the region of interest. Taking the detection relating to the oculi anterior as an example, if the measurement area is too close to the crystalline lens, light scattering from the crystalline lens will be picked up as noise which will affect the results.

To reduce or eliminate the effects of such noise, in the apparatus described in Japanese Patent Public Disclosure No. 135128/88 the laser beam is made to overscan the mask aperture and the noise component is eliminated by obtaining the difference between the signal obtained from the photosensor when the laser beam is within the limits of the aperture and the signal obtained when the beam is outside the aperture.

The human cornea has a strong lens effect which causes incident light that is not along the normal line to be refracted at the cornea surface. Hence, when the area on which the light impinges changes, the degree of refraction also changes, disturbing the relationship between the measurement area (point of laser beam convergence) and the aperture of the mask of the light receiving section.

With the depth of the aqueous humor in the oculi anterior being around 3 mm, the laser has to be focused on a median portion at a depth of 1 mm to 2 mm and the light scattered from this measurement area has to be accurately captured. This requires accurate alignment of the apparatus with the patient's eye, particularly in the horizontal plane, and a method of achieving this alignment accurately. Failure to align the system prior to carrying out measurements will result in the entry into the measurement mask aperture of various harmful light rays from areas other than the measurement area concerned, making it impossible to obtain accurate measurements.

Elimination of the harmful light rays has conventionally been confirmed by visual observation of the person making the measurement. The harmful rays are very weak, however, and when their intensity approaches that of scattered light, this confirmation becomes difficult.

SUMMARY OF THE INVENTION

An object of the present invention is therefore to provide an ophthalmological measurement apparatus which ensures accurate ophthalmological measurements by eliminating harmful light rays from areas other than the measurement area concerned.

In accordance with the present invention, the above object is achieved by an ophthalmological measurement apparatus wherein ophthalmological measurement is performed by projecting a laser beam at a selected point in a subject's eye and detecting the light scattering therefrom, comprising:

laser beam projection means for converging a laser beam from a laser source at a measurement point in the eye; light receiving means having a photosensor for receiving scattered laser light from the measurement point via a mask with an aperture of a prescribed size provided at a position that is a conjugate of the point of convergence of the laser beam; means for deflecting the laser beam in a prescribed direction for scanning of the measurement zone beyond the size of the aperture during alignment of the apparatus with the eye and during measurement; and processing means for performing the ophthalmological measurement by processing signals received from the light receiving means whereby; high-speed laser beam scanning of the measurement zone is implemented during alignment using a scanning width that is the same as the scanning width used for the measurement and the signal obtained from the photosensor at this time is processed to provide information on and an indication of the appropriateness of the state of alignment.

With the above arrangement, during alignment the laser beam is deflected and performs high-speed scanning of the measurement zone at the same scanning width used for measurement scanning. A conjugate relationship is established between the point of convergence and the measurement mask and between the measurement mask and the alignment index so that when the alignment index is guided to the measurement area of the patient's eye, it becomes possible to carry out rough alignment in which harmful (noise) light rays can be eliminated to some degree by visual observation. On the other hand, the appearance of the alignment index is caused to change depending on whether or not processing of the output signal from the light receiving section shows the predetermined conditions to be satisfied, so that the person conducting the examination (the examiner) can learn whether or not weak noise that would be difficult for him or her to confirm visually is present.

Thus the present invention enables the examiner to know prior to the measurement whether or not the alignment is appropriate and is thus highly effective for carrying out error-free measurement in less time and with less burden on the patient.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENTS

Figure 1:
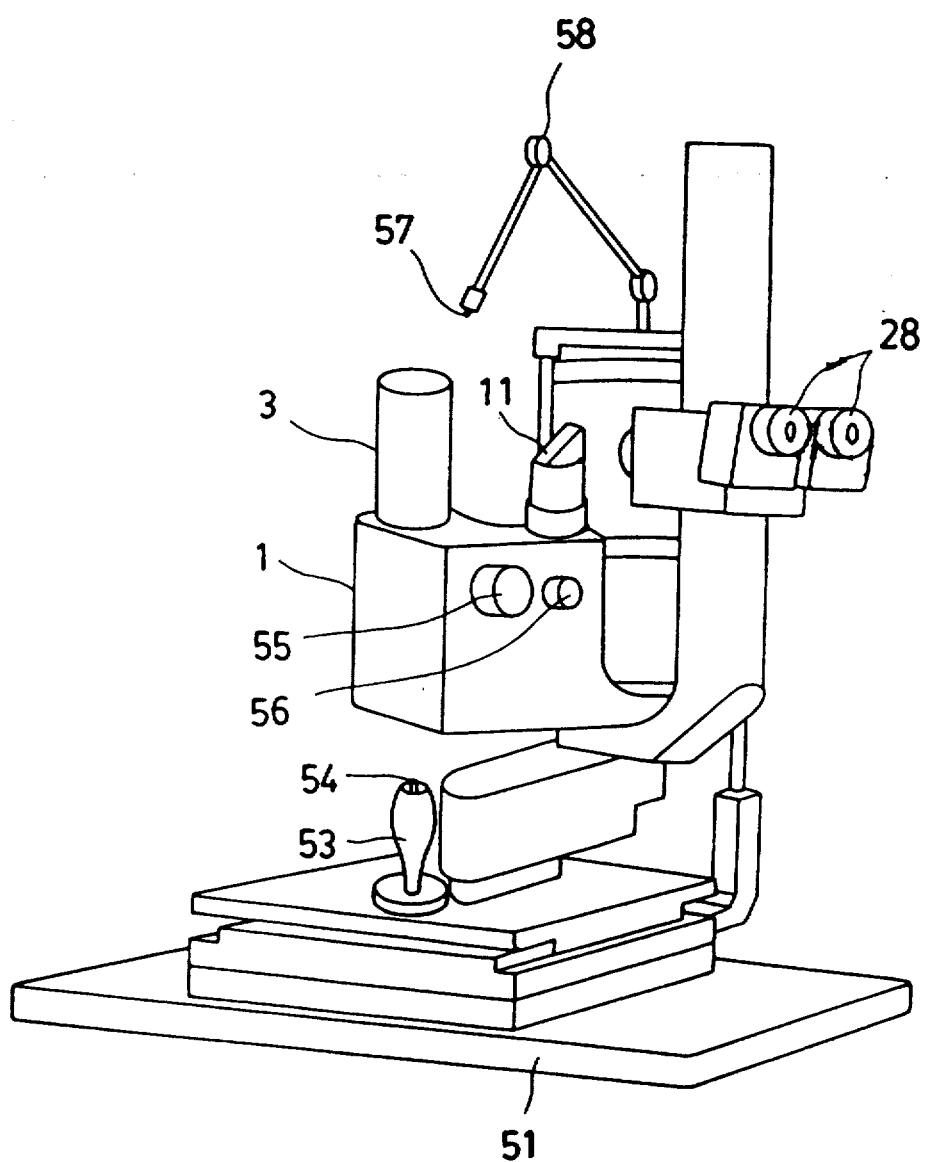
FIG. 1 is a perspective view of the ophthalmological measurement apparatus of the present invention.

The invention will now be described in detail on the basis of the preferred embodiments illustrated in the drawings.

Figure 2:
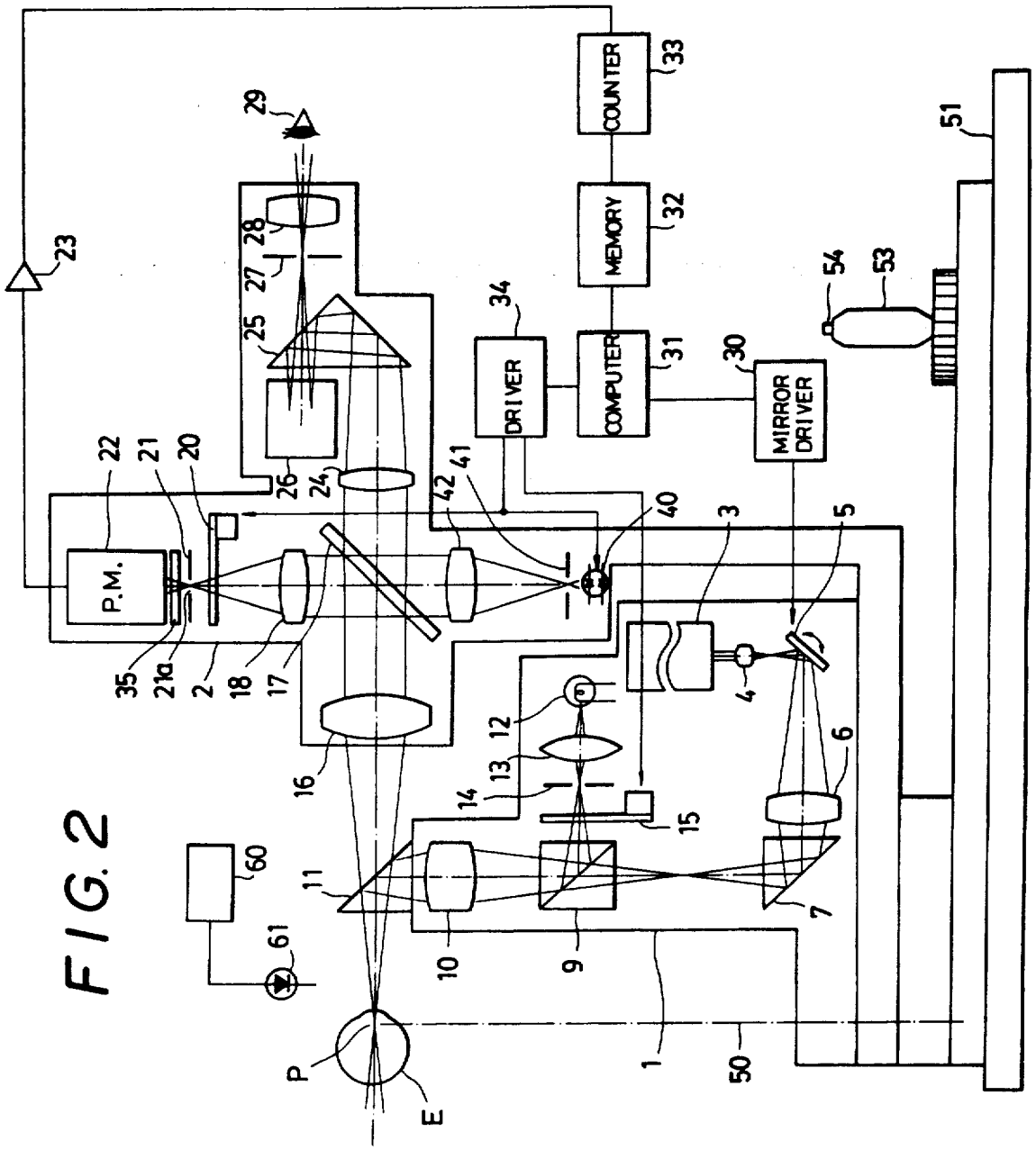
FIG. 2 is a schematic view of the internal configuration of the projection section of the apparatus shown in FIG. 1.
Figure 3:
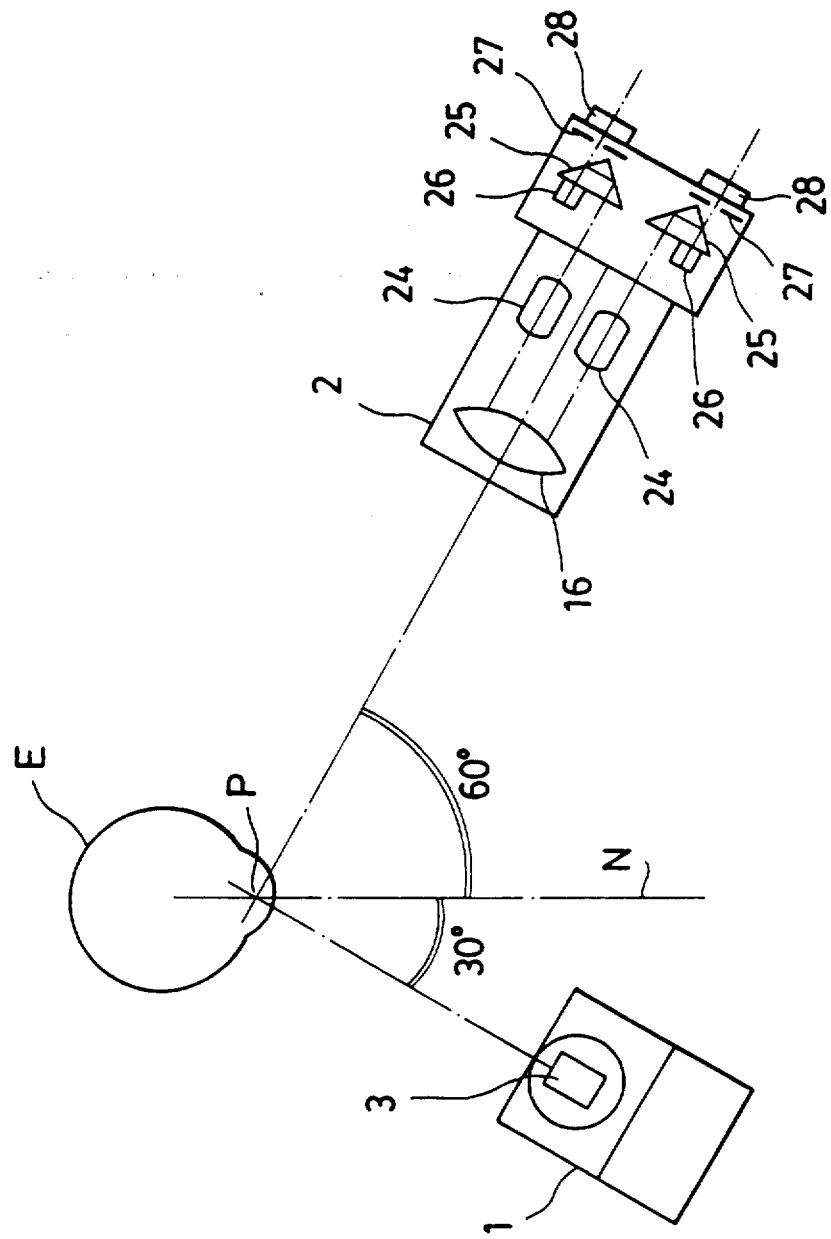
FIG. 3 shows the positional relationship between the light projection section and the light receiving section during measurement.

FIGS. 1 to 3 show the general configuration of an embodiment of the ophthalmological measurement apparatus of this invention. In the drawings reference numeral 1 denotes a laser light projection section having a helium-neon or other such laser light source 3. The laser beam from the laser light source 3 passes through a lens 4, a movable mirror 5, a lens 6, a prism 7, a beam-splitter 9, a lens 10 and a prism 11 whereby the beam is converged on a prescribed point P in the oculi anterior of the eye E being examined.

The movable mirror 5 is connected to a mirror drive circuit 30 controlled by a computer 31 constituted by a microprocessor or the like in a configuration that allows the angle of the movable mirror 5 to be changed so as to deflect the laser beam to scan a measurement zone over a prescribed range about a center formed by a point of laser beam convergence P. As described below, this scanning range is set so that it exceeds the range of an aperture formed in a measurement mask.

The laser light projection section 1 is provided with a white-light source 12 (a halogen lamp), light from which illuminates a slit 14 via a lens 13. The light from the slit 14 thus illuminated passes via a slit light shutter 15, the beam splitter 9, the lens 10 and the prism 11 to form a slit image in the vicinity of the point of convergence P in the oculi anterior of the eye E.

By illuminating the area around the point of convergence P, the slit image allows the position of the point of convergence P to be readily confirmed when the system is being aligned.

The width and length of the slit 14 can be adjusted by a slit width adjustment knob 55 and slit length adjustment knob 56 (FIG. 1) to enable the apparatus to be utilized also as a slit-lamp microscope.

The computer 31 controls the shutter 15 via a drive circuit 34 so that the shutter 15 is open during alignment and closed during measurement of protein concentration in the oculi anterior. This is accomplished by inserting the shutter 15 into, or retracting it from, the corresponding optical system by operating an input device such as a joystick 53 which is equipped with a push-button switch 54 and provided on a base 51.

Figure 6:
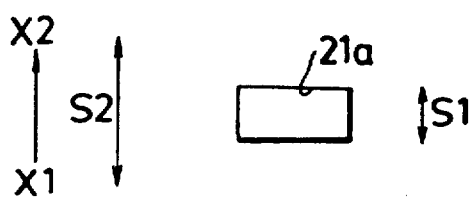

A light receiving section 2 is provided for receiving scattered light from the vicinity of the point of convergence P and to allow the area to be observed. For this, scattered light from the point of convergence P in the oculi anterior of the eye E under examination passes through a lens 16, is reflected by a semi-transparent mirror 17 and passes, via a lens 18, a photomultiplier shutter 20, a measurement mask 21 and a bandpass filter 35 to impinge on a photomultiplier (P.M.)22 which constitutes the photosensor. Light impinging on the photomultiplier 22 is limited to light passing through an aperture 21a formed in the mask 21, which therefore serves to block extraneous light from other areas. The measurement mask 21 (aperture 21a) is provided at a position that is optically conjugate with the point of convergence P, with respect to the light receiving section 2. The aperture 21a is rectangular in shape, as can be seen in FIG. 6.

The bandpass filter 35 is provided for allowing only the laser light to pass to the photomultiplier 22, while shutting out the white light from the white-light source 12, which constitutes noise, as much as possible.

The output from the photomultiplier 22 is passed through an amplifier 23 and input to a counter 33 which counts the intensity of the scattered light detected by the photomultiplier 22 as a pulse count per unit time. The count values for each unit time as counted by the counter 33 are stored at specific locations in a memory 32. The data thus stored in the memory 32 is arithmetically processed by the computer 31 to compute the appropriateness of the alignment and the protein concentration in the oculi anterior.

The shutter 20 is provided to protect the photomultiplier 22 and is open only during measurement. Like the shutter 15 it is inserted into, or retracted from, the corresponding optical system by the drive circuit 34 operated in conjunction with the oscillation of the movable mirror 5 by an input device such as the joystick 53 equipped with a push-button switch 54.

Provided to the rear of the semi-transparent mirror 17 of the light receiving section is a microscope system which permits observation around the point of convergence P in the eye. With this configuration, light transmitted through the semi-transparent mirror 17 is observed by an examiner 29 via a lens 24, erect normal prisms 25 and 26, field of vision stop 27 and eyepiece 28. As shown in FIG. 3 the microscope is provided with a double eyepiece for binocular viewing. The microscope allows the projected laser beam and the origin of harmful light rays to be observed prior to measuring the protein concentration in the oculi anterior. To enable harmful light rays to be determined as accurately as possible during system alignment, in this embodiment (as described below in further detail) the measurement zone is scanned at a higher frequency during the alignment than the frequency of the measurement scanning, thus permitting alignment by visual observation, and, moreover, the output from the photomultiplier is processed for detecting the presence/absence of weak harmful light rays and thus making it possible for the examiner to know the appropriateness of the alignment.

The light receiving section 2 is also provided with an alignment index 41 which is illuminated by a light-emitting diode (LED) or other such alignment light source 40. The alignment index 41 is located at a position that is conjugate with the mask 21 and with the field of vision stop 27. Thus, the point of convergence P is conjugate with respect to the mask 21 and field of vision stop 27, and the alignment index 41 is also conjugate with respect to the mask 21 and field of vision stop 27. The alignment light source 40 is constituted of an LED that emits light of two colors and is driven by the same driver circuit 34 that drives the shutters 15, 20 so as to emit light of one color when the alignment is appropriate, to emit light of the other color when the alignment is inappropriate and to be turned off during measurement.

An eye fixation light 57 constituted, in this embodiment, by a light-emitting diode is provided at a position that permits the examiner to fix the patient's eye (FIG. 1). The eye fixation light 57 can be turned in the direction indicated by the arrow by means of a linkage 58 to enable it to be adjusted to the optimal position relative to the patient undergoing the eye examination. The light selected for the eye fixation light 57 is of a different color than the laser light.

Provided on the base 51 is an input means, which in this case is the joystick 53 equipped with a push-button 54. This input means can be used for moving optical elements such as the shutters 15 and 20 into and out of the respective optical system as described above, or may be used to switch the alignment light source on and off. The laser light projection section 1 and light receiving section 2 can each rotate independently in a horizontal plane about an axis 50. With reference to FIG. 3, when the protein concentration in the oculi anterior is being measured, a detent mechanism or the like is used to lock the laser light projection section 1 and the light receiving section 2 at an angle of 30 degrees and 90 degrees respectively with respect to the normal of the corneal vertex. When the apparatus is to be used as a slit-lamp microscope the two sections are unlocked to allow them to rotate freely to view the eye in cross-section.

A power supply 60 (FIG. 2) is provided for supplying power to the various components and circuitry. A lamp 61 indicates when the power supply 60 is on.

The overall operation of the apparatus thus configured will now be described. The patient's head is positioned on a chin rest, the white-light source 12 is switched on and the shutter 15 is opened to project an image of the slit 14 onto the eye E. The laser beam from the laser light projection section 1 is converged on the point of convergence P in the eye E, and the mirror driver circuit 30, upon being actuated by an input device such as the push-button switch 54, functions to oscillate the movable mirror 5 so that the laser beam scans the measurement zone at high speed about a center formed by the point of convergence P. The photomultiplier shutter 20 is left open during the alignment procedure. Here, as shown in FIG. 6, the scanning width S2 at the measurement area is set to about twice the width S1 of the image of the mask aperture 21a in the eye. The scanning frequency used is 50 to 60 Hz, for instance, which is high enough to permit observation of the measurement zone by the human eye without any perception of flicker.

Figure 4:
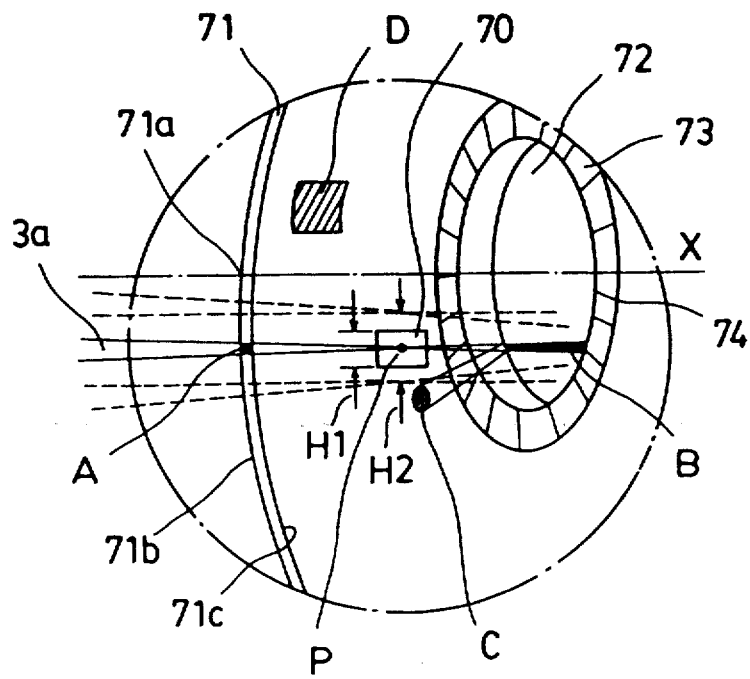
FIG. 4 is an explanatory view of the observed origin of harmful light rays.

Next, the alignment light source 40 is switched on to illuminate the alignment index 41. The image that the examiner will see at this point is shown in FIG. 4. The point of convergence P is at a position that is conjugate with the mask 21 and the field of vision stop 27, while the alignment index 41 is in a conjugate relationship with the mask 21 and field of vision stop 27. To the examiner 29, therefore, the alignment index 41 illuminated by the light source 40 appears to be located at the point of convergence P.

Figure 5:
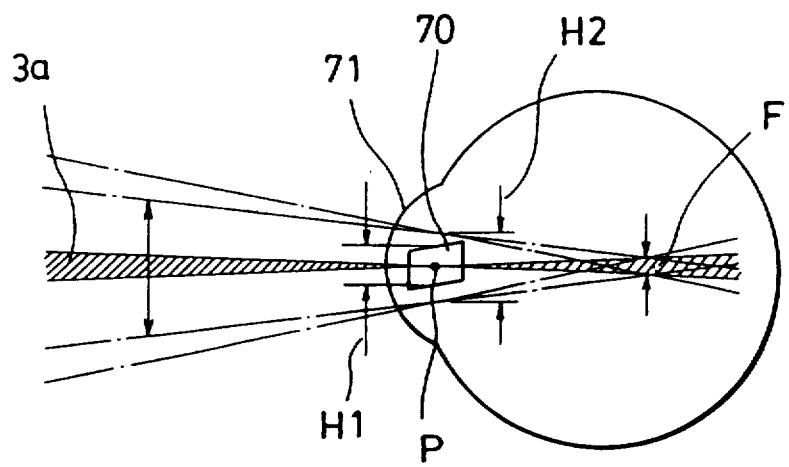
FIGS. 5 and 6 are explanatory views illustrating the range of deflection of the laser beam.

When an arrangement is used whereby the size and shape of the alignment index 41 is such that the image of the alignment index on the mask 21 coincides with the aperture 21a, to the examiner it will appear that the aperture 21a is highlighted at the point of convergence P. In FIGS. 4 and 5 this image of the rectangular aperture 21a is denoted by the reference number 70. With reference to FIG. 4, which shows what is actually observed via the eyepiece 28, the aperture image 70 is shown more or less in the middle of the field of vision slightly below the center line X that passes through the corneal vertex 71a. To simplify the explanation, in FIG. 5 the center of the aperture image 70 is shown as coinciding with the vertex of the cornea 71.

In this embodiment the movable mirror 5 scans the laser beam 3a over a range that is about twice the width of the image 70 of the aperture 21a. In the drawings (FIGS. 4 and 5) in which H2 is the range of a measurement zone scan sweep by the laser beam 3a and H1 is the length of the aperture image 70 measured along the short side, H2 is about twice H1. In FIG. 5, F is a point at which there is no movement even during deflection of the laser beam 3a. There is no movement at F because it is conjugate with respect to the axis of oscillation of the reflecting surface of the movable mirror 5, and therefore the oscillation of the movable mirror 5 has no bearing on it.

With reference to FIG. 4, light rays originating in an area outside the aperture image 70 will be unable to pass through the mask 21, and it thus becomes possible to block them by suitably causing the sources of harmful rays of light present within the cornea and the crystalline lens to fall outside the area of the mask aperture image 70. Light rays harmful to the measurement are described below.

The laser beam 3a impinges on the cornea 71 before reaching the point of convergence P and is scattered from the part of the cornea 71 marked A. (Although slit and laser light is actually scattered from two points, the front surface 71b and rear surface 71c of the cornea 71, because of the closeness of the two in the drawing they are shown as a single point A.) The laser beam 3a also passes through the point of convergence P and into the crystalline lens 72 where it produces scattered light B. Moreover, light reflected by the surface of the crystalline lens 72 forms an image C on the cornea 71. This harmful light B and C is particularly intense in the case of a prosthetic crystalline lens. In FIG. 4, 73 is the iris. The boundary between the iris 73 and the crystalline lens 72 forms the pupil 74. At D, a corneal image is formed by scattered light from the exit face of the prism 11. Specifically, as the laser light passes through the prism 11 and converges in the eye, it is scattered at the exit face of the prism, producing secondary light sources that give rise to a spurious image owing to the convex mirror effect of the cornea.

The above A to D are the main sources of harmful rays. For making it possible to distinguish these harmful rays during alignment, in this embodiment, during the alignment the laser beam 3a is made to scan the measurement zone at high speed at the same scan width (H2) used for measurement scanning. Since this high-speed scanning of the measurement zone is performed at a frequency such as 50 Hz or 60 Hz that is above the flicker perception threshold of the human eye, it becomes possible to simulate the harmful light rays arising during actual measurement, which facilitates the identification and elimination of the harmful rays.

The elimination of the harmful light rays A to D is realized by aligning the apparatus so that the rays do not come within the aperture image 70. As these harmful light rays behave like scattered light sources with low directivity and illuminate the surrounding area, in order to ensure that only scattered light from proteins in the oculi anterior is received, the system should be aligned to achieve a maximum separation of the aperture image 70 from the harmful light sources to optimize measurement precision. When the system is aligned in this manner, it becomes possible to receive solely the light scattered by the protein in the oculi anterior and thus to increase the accuracy of the measurement. However, while stronger harmful rays can be can be easily discerned by visual observation, the secondary and tertiary harmful rays are extremely weak and virtually impossible to discern visually.

Figure 7:
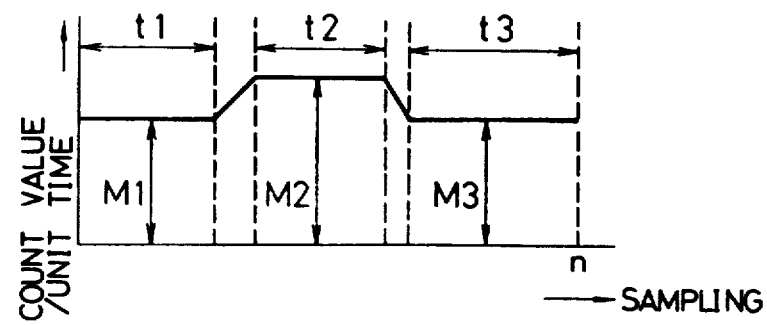
FIG. 7 is a waveform of a signal obtained from one sweep of the scanning laser beam.

In this invention, therefore, the output signal of the photomultiplier is processed during alignment in the same manner as during measurement (to be described below) and it is judged that the alignment is such as to eliminate the influence of harmful rays when, as shown in FIG. 7, M1 and M3 are smaller than M2 and, moreover, M1 and M3 are substantially equal. Upon receiving the judgment to this effect, the drive circuit 34 changes the color of the light emitted by the light source 40, thus indicating to the examiner that the alignment is proper so that he may proceed with the measurement.

Alternatively, it is possible to use other methods of indicating the appropriateness of the alignment than that used in the present embodiment. For example, as the light source 40 for illuminating the alignment index 41 there can be used a monochrome LED which is made to flash at a low frequency (e.g. 1-2 Hz) when the alignment is inappropriate, to flash at progressively higher (but visibly perceptible) frequencies as the alignment improves and to become constantly on when the alignment becomes proper for measurement. With this method, the examiner is able to conduct the alignment more easily than in the aforesaid embodiment since he is supplied with information regarding the degree of appropriateness of the alignment.

In accordance with another embodiment, the examiner can be informed of the appropriateness of the alignment by a synthesized voice or the like.

If the output of the photomultiplier should be too weak during alignment conducted in accordance with the method described below, an adequately strong output can be obtained by integrating the signals obtained during a plurality of scan sweeps.

Further, if the two colors of the light for illuminating the alignment index are made different from the color of the laser light (e.g. yellow and green in the case of a red laser beam), the mask aperture image 70 can be readily distinguished from the harmful light ray sources A to D.

Preferably, the aperture image 70 in the eye should have a width that is about one-thirtieth to one-fifteenth the diameter of the dilated pupil and a length that is one-eighth to one-quarter the depth of the oculi anterior.

After the above alignment is accomplished, the system mode is changed to measurement. In measurement mode, pressing the switch 54 of the joystick 53 turns off the alignment light source 40, causes scanning of the measurement area to be conducted at a different frequency than during alignment, and enables scattered laser light to be received by the light receiving section 2 and measured to determine the protein concentration in the oculi anterior.

During the measurement process the projection section 1 projects the beam of laser light at the point of convergence P of the eye E under examination and light scattering from the area around the point of convergence P is received by the photomultiplier 22 of the light receiving section 2. The movable mirror 5 is oscillated by the mirror drive circuit 30 in the direction shown by the arrow to scan the measurement zone with point P at the center. As there is no need to eliminate flicker during measurement scanning, the laser beam 3a is deflected at a lower frequency setting of about 2 Hz, which makes it possible to secure a signal adequate for obtaining a measurement result with a good signal/noise ratio (FIG. 6).

The photomultiplier 22 receives incident scattered laser light via the aperture 21a and detects the intensity of the light scattered by protein particles in the measurement zone of the oculi anterior and outputs a corresponding signal. The scattered light intensity signal is converted to a corresponding pulse train and counted by the counter 33 as a pulse count per unit time period, and the count values per unit time are stored at specific locations in the memory 32. As described earlier and shown in FIG. 6, when each scan of the laser beam 3a extends from x1 to x2 and the count values for n scans have been stored at respective memory locations, the count values stored in the memory 32 become as shown in FIG. 7 when arranged in time sequence.

With reference to FIG. 7, t1 and t3 are intervals when the incident laser beam 3a strikes the mask at opposite sides of the aperture 21a and is not within the aperture 21a. During the intervals t1 and t3, the output signals (side signals) of the photomultiplier 22 contain extraneous; noise components produced by intra-ocular reflection or scattering of light other than the aforesaid harmful rays, or the ambient brightness of the measurement environment. M1 and M3 are taken as average values of counts in the memory 32 for intervals t1 and t3. Also included as noise in M1 and M3 is the dark current of the photomultiplier 27. These noise components fluctuate from measurement to measurement and constitute extraneous noise.

Interval t2 is the interval during which the scattered laser light enters via the aperture 21a and the output signal (main signal) of the photomultiplier 22 includes signal components corresponding to the protein concentration in the oculi anterior and extraneous noise such as noise components caused by reflection and scattering, noise components caused by the ambient brightness, and the photomultiplier dark current. M2 is the average of the count values stored in the memory 32 during this interval.

Figure 8A:
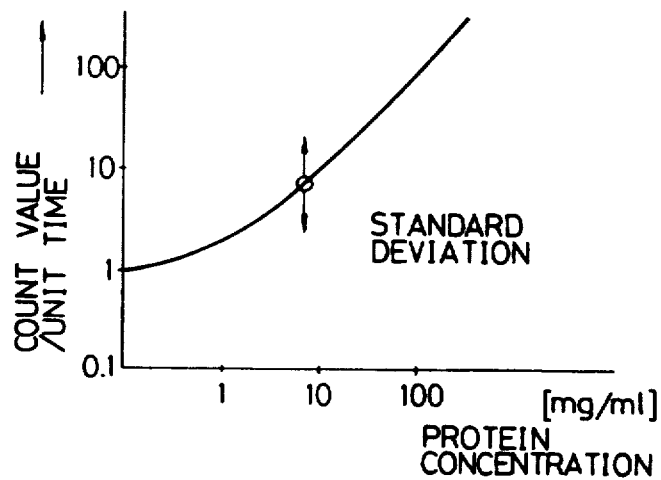
FIGS. 8a and 8b are characteristic curves plotted from data values obtained at different scanning widths.
Figure 8B:
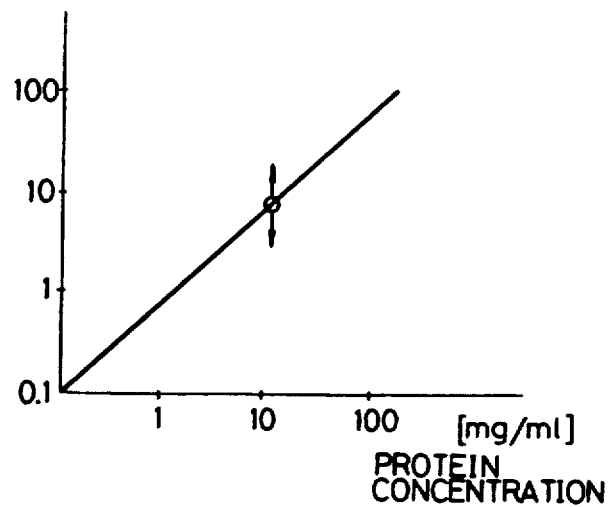

The computer 31 deducts the mean value of M1 and M3 from the value M2 stored in the memory 32 to extract the effective component, from which it computes the protein concentration in the oculi anterior. If the system has been properly aligned, the values of M1 and M3 will be about the same. If the data were only obtained by measurement during the interval t2, the signal/noise ratio would be poor and the variance large with a corresponding degradation in reproducibility (FIG. 8a) but, as shown by FIG. 8b, in accordance with this invention the signal/noise ratio is improved by deducting the noise component, which also increases the dynamic range and improves the reproducibility.

Thus, in accordance with the present invention, high-speed laser beam scanning of the measurement zone is implemented during alignment using a scanning width that is the same as the scanning width used for the measurement. Thus during alignment it is possible to observe any harmful light rays that will actually appear during measurement, and, moreover, the output of the photomultiplier during alignment can be processed for providing an indication showing the appropriateness of the alignment. This enables the apparatus to be aligned so that the harmful light rays do not come within the measurement mask aperture, thereby enabling measurement to be conducted under optimum conditions.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmological measurement apparatus wherein ophthalmological measurement is performed by projecting a laser beam at a selected point in a subject's eye and detecting the light scattered therefrom, comprising:
    laser beam projection means for projecting and converging a laser beam from a laser source at a measurement point in a subject's eye;
    a mask having an aperture of a prescribed size and disposed at a position that is a conjugate of the point of convergence of the laser beam;
    means for deflecting the laser beam in a prescribed direction for scanning a measurement zone beyond the size of the mask aperture during alignment of the apparatus with the eye and during measurement so that during each scan, the laser beam sequentially strikes the mask at one side of the aperture, passes through the aperture, and strikes the mask at the other side of the aperture;
    light receiving means including a photosensor operative during both alignment and measurement for receiving, during the portion of each scan when the laser beam passes through the aperture, scattered laser light from the measurement point and noise light to produce therefrom a main signal and for receiving, during the portions of each scan when the laser beam strikes the mask at opposite sides of the aperture, noise light to produce therefrom respective side signals; and
    processing means operable during alignment for processing the main and side signals to produce information indicative of the state of alignment and operable during ophthalmological measurement for processing the main and side signals to produce ophthalmological information.

2. An ophthalmological measurement apparatus as set forth in claim 1, wherein an alignment index is disposed at a position conjugate with the aperture and is indicated in one color when the alignment is appropriate and in another color when it is inappropriate.

3. An ophthalmological measurement apparatus as set forth in claim 1, wherein an alignment index is disposed at a position conjugate with the aperture and is caused to flash at one frequency when the alignment is appropriate and at another frequency when it is inappropriate.

4. An ophthalmological measurement apparatus as set forth in claim 2, wherein the two different colors of the alignment index are obtained using a light-emitting diode capable of producing light of two colors.

5. An ophthalmological measurement apparatus as set forth in claim 1, wherein the signals obtained during alignment are integrated.

6. An ophthalmological measurement apparatus as set forth in any of claims 1 to 5, wherein a bandpass filter that passes only light of the wavelength of the laser beam is disposed in the optical path of the photomultiplier.

7. An ophthalmological measurement apparatus, comprising: means for projecting a beam of laser light onto a measurement point in an eye of a person to be examined whereby the eye scatters the laser light; a mask having an aperture of prescribed size and positioned to receive therethrough the scattered laser light and other extraneous light; deflecting means for deflecting the beam of laser light in a scanning direction to scan the beam over a prescribed measurement zone in the eye which includes the measurement point, the measurement zone being larger in size in the scanning direction than that of the aperture so that each scan of the beam causes scattered laser light to scan across the mask and sequentially strike the mask at one side of the aperture in a first interval, pass through the aperture in a second interval, and strike the mask at the other side of the aperture in a third interval; light receiving means disposed behind the mask aperture for receiving during each scan extraneous light during the first interval, scattered laser light and extraneous light during the second interval, and extraneous light during the third interval and producing output signals corresponding to the intensity of light received during each interval; and processing means for processing the output signals in an alignment mode to produce alignment information indicative of the state of alignment of the eye and apparatus and for processing the output signals in a measurement mode to produce measurement information indicative of a property of the eye.

8. An ophthalmological measurement apparatus according to claim 7; wherein the deflecting means includes means for deflecting the beam of laser light the same extent in the scanning direction during both alignment and measurement.

9. An ophthalmological measurement apparatus according to claim 8; wherein the scanning extent is substantially twice as long as the aperture in the scanning direction.

10. An ophthalmological measurement apparatus according to claim 7; wherein the deflecting means includes means for deflecting the beam of laser light at a higher frequency during alignment than during measurement.

11. An ophthalmological measurement apparatus according to claim 10; wherein the scanning frequency during alignment is high enough to prevent a flicker effect when the measurement zone is observed by a human eye.

12. An ophthalmological measurement apparatus according to claim 7; including an alignment index disposed at a position conjugate with the mask aperture so that an image of the alignment index appears superimposed on an image of the measurement zone formed at the mask aperture during alignment.

13. An ophthalmological measurement apparatus according to claim 12; including means connected to the processing means for changing the color of the alignment index image depending on the state of alignment.

14. An ophthalmological measurement apparatus according to claim 12; including means connected to the processing means for flashing the alignment index image at different frequencies depending on the state of alignment.

15. An ophthalmological measurement apparatus according to claim 7; wherein the processing means includes means for integrating the output signals during alignment and processing the integrated signals to produce alignment information.

* * * * *